(12) United States Patent
Miyake et al.

(10) Patent No.: US 11,767,282 B2
(45) Date of Patent: Sep. 26, 2023

(54) COMPOSITION BIOLOGICALLY ACTIVE TO STENOMA CATENIFER AND SUSTAINED RELEASE PREPARATION COMPRISING THE SAME FOR CONTROLLING INSECT PEST

(71) Applicant: Shin-Etsu Chemical Co., Ltd., Tokyo (JP)

(72) Inventors: Yuki Miyake, Joetsu (JP); Tatsuya Fujii, Tokyo (JP); Yasuhiko Kutsuwada, Joetsu (JP); Takeru Watanabe, Joetsu (JP); Takeshi Kinsho, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 17/848,592

(22) Filed: Jun. 24, 2022

(65) Prior Publication Data

US 2022/0411358 A1    Dec. 29, 2022

(30) Foreign Application Priority Data

Jun. 28, 2021  (JP) .................................. 2021-106294

(51) Int. Cl.
| | | |
|---|---|---|
| *C07C 47/21* | (2006.01) | |
| *C07C 47/222* | (2006.01) | |
| *A01N 31/04* | (2006.01) | |
| *A01P 19/00* | (2006.01) | |
| *A01N 35/02* | (2006.01) | |
| *C07C 47/20* | (2006.01) | |

(52) U.S. Cl.
CPC ............ *C07C 47/222* (2013.01); *A01N 31/04* (2013.01); *C07C 47/21* (2013.01)

(58) Field of Classification Search
None
See application file for complete search history.

(56) References Cited

PUBLICATIONS

Pierre; et al., Sex pheromone of Stenoma cecropia Meyrick Lepidoptera: Elachistidae), J. of Chemical Ecology (1996), 22(6), (Year: 1996).*

Tellier, et al., Stereospecific synthesis of (Z,E)-9,11,13-tetradecatrien-1-yl acetate and aldehyde sex pheromone components of Stenoma cecropia and Ectomyelois ceratoniae, Tetrahedron Letters (1990), 31(16), 2295-8 (Year: 1990).*

Millar, (9Z)-9,13-tetradecadien-11-ynal, the sex pheromone of the avocado seed moth, Stenoma catenifer, Tetrahedron Letters, (Aug. 11, 2008) vol. 49, No. 33, pp. 4820-4823 (Year: 2008).*

Cabrera et al. "Sex Pheromone of Tomato Fruit Borer, Neoleucinodes elegantalis" Journal of Chemical Ecology, 27 (10):2097-2107 (2001).

Hoddle et al. "Synthesis and Field Evaluation of the Sex Pheromone of Stenoma catenifer (Lepidoptera Elachistidae)" Journal of Economic Entomology, 102(4):1460-1467 (2009).

Karg et al. "Applied Aspects of Insect Olfaction" Insect Olfaction, Chapter 12, pp. 352-377 (1999).

Millar et al. "(9Z)-9,13-Tetradecadien-11-ynal, the sex pheromone of the avocado seed moth, Stenoma catenifer" Tetrahedron Letters, 49(33):4820-4823 (2008).

* cited by examiner

*Primary Examiner* — Alton N Pryor
(74) *Attorney, Agent, or Firm* — Myers Bigel, P.A.

(57) ABSTRACT

There are provided a composition which has a larger attracted number than (9Z)-9,13-tetradecadien-11-ynal alone; and others. More specifically, there are provided a composition bioactive to *Stenoma catenifer* (STENCA), the composition including (9Z)-9,13-tetradecadien-11-ynal and (9E)-9,13-tetradecadien-11-ynal; a sustained release preparation for controlling STENCA, the preparation including the composition and a carrier or container for sustainedly releasing the (9Z)-9,13-tetradecadien-11-ynal and the (9E)-9,13-tetradecadien-11-ynal; and a method for controlling STENCA, the method including a step of installing the sustained release preparation in a field to release the (9Z)-9,13-tetradecadien-11-ynal and the (9E)-9,13-tetradecadien-11-ynal into the field.

6 Claims, 1 Drawing Sheet

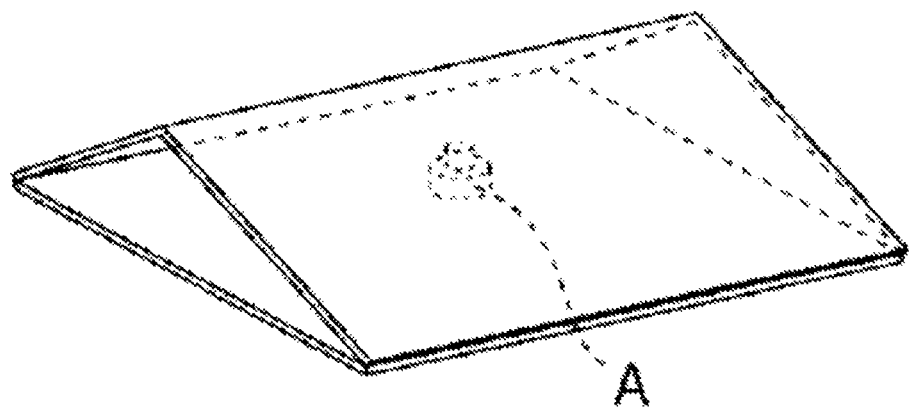

COMPOSITION BIOLOGICALLY ACTIVE TO STENOMA CATENIFER AND SUSTAINED RELEASE PREPARATION COMPRISING THE SAME FOR CONTROLLING INSECT PEST

BACKGROUND OF THE INVENTION

1. Field of the Invention

The invention relates to a composition bioactive to *Stenoma catenifer*, and a sustained release preparation comprising the same for controlling an insect pest.

2. Related Art

Avocado seed moth is the most significant insect pest of avocados in Latin America including Mexico, Guatemala, Peru, Ecuador and Brazil, and creates a major problem for directly damaging the fruits. For example, in some areas of South America, pesticides are sprayed seven to eleven times per season, but 60% of the fruits are said to be damaged. One of the reasons for this is that the larvae of the insect pest penetrate into the fruit pulps, thereby making it difficult to control them by an insecticide. For such reasons, biological controls are attracting attention, and as one of the biological controls, the control using a sex pheromone substance is expected.

Examples of the methods for controlling an insect pest by using a sex pheromone substance include "mass trapping" and "attract and kill", where adult insects are captured or killed by gathering them at a certain place with a pheromone attractant to reduce the density of insect pests in the field; "push-pull" in which insect pests are captured or killed after moving into a certain direction to reduce the density of insect pests in the field by using a pheromone attractant and a repellent; "attract and infect" in which adult insect pests are attracted by a pheromone attractant, infected with pathogens, and then released in the field to infect insect pests of interest with the pathogens to lower the density of insect pests in the field; and "mating disruption" in which pheromone preparations are installed in the field to prevent the insect pests from finding mating partners, thereby lowering the density of insect pests of the next generation (see B. S. Hansson (Editor), Insect Olfaction, Chapter 12 "Applied Aspects of Insect Olfaction", pages 352-377).

In any of the above methods for controlling an insect pest, an attractive composition capable of attracting a large number of target insect pests with high accuracy is important.

A sex pheromone of *Stenoma catenifer* has been reported to be (9Z)-9,13-tetradecadien-11-ynal (see Jocelyn G. Millar et al., Tetrahedron Letters 2008, 49, 4820-4823, and Mark S. Hoddle et al., J. Econ. Entomol. 2009, 102(4), 1460-1467).

SUMMARY OF THE INVENTION

According to Mark S. Hoddle et al., the composition containing (9Z)-9,13-tetradecadien-11-ynal as a sole bioactive component had the highest activity among the many attractant compositions used in the field test, and was confirmed to have the attraction activity to males. However, Mark S. Hoddle et al. admitted that the attracted number itself was small so that the attraction activity was insufficient. Thus, in order to put an attractant composition in practical use, there has been a strong demand for an attractive composition having even slightly higher activity than the conventional compositions in consideration of severe agricultural damages caused by *Stenoma catenifer*.

In view of the above circumstances, the invention has been made. An object of the invention is to provide a composition capable of attracting a large number of insect pests than (9Z)-9,13-tetradecadien-11-ynal alone, and a sustained release preparation comprising the composition for controlling an insect pest.

As a result of extensive studies to achieve the object, the inventors have found that the addition of (9E)-9,13-tetradecadien-11-ynal, which is a geometric isomer of (9Z)-9,13-tetradecadien-11-ynal, which is an *Stenoma catenifer* sex pheromone, increases the attracted number, and have completed the invention. In this specification, (9Z)-9,13-tetradecadien-11-ynal and (9E)-9,13-tetradecadien-11-ynal are given the numbers (1) and (2), respectively, for clarity.

In one aspect of the invention, there is provided a composition bioactive to *Stenoma catenifer*, the composition comprising (9Z)-9,13-tetradecadien-11-ynal (1) and (9E)-9,13-tetradecadien-11-ynal (2).

In another aspect of the invention, there is provided a sustained release preparation for controlling *Stenoma catenifer*, the preparation comprising the composition and a carrier or container for sustainedly releasing the (9Z)-9,13-tetradecadien-11-ynal (1) and the (9E)-9,13-tetradecadien-11-ynal (2).

In still another aspect of the invention, there is provided a method for controlling *Stenoma catenifer*, the method comprising a step of installing the sustained release preparation in a field to release the (9Z)-9,13-tetradecadien-11-ynal (1) and the (9E)-9,13-tetradecadien-11-ynal (2) into the field.

According to the invention, it is possible to provide a composition which specifically attracts a larger number of male adults of *Stenoma catenifer* and is effective for more detailed emergence information. Further, it is also possible to directly control *Stenoma catenifer* through mass trapping, mating disruption and others by using the sustained release preparation comprising the composition.

BRIEF DESCRIPTION OF THE DRAWINGS

FIG. 1 shows a white sticky type trap.

DETAILED DESCRIPTION OF THE PREFERRED EMBODIMENTS

First, a composition bioactive to *Stenoma catenifer* comprising (9Z)-9,13-tetradecadien-11-ynal (1) and (9E)-9,13-tetradecadien-11-ynal (2) will be described.

It has been reported that as a result of pheromone gland extraction and GC-EAD (GC-electroantennogram detection) of *Stenoma catenifer*, three compounds, (9Z)-9,13-tetradecadien-11-ynal (1), (9Z)-9,13-tetradecadien-11-yn-1-ol, (6Z,9Z)-6,9-tricosadiene are pheromone candidate compounds (Jocelyn G. Millar et al., Tetrahedron Letters 2008, 49, 4820-4823). In addition, the field attraction tests using these three compounds revealed that (9Z)-9,13-tetradecadien-11-ynal (1) attracted *Stenoma catenifer*; (9Z)-9,13-tetradecadien-11-yn-1-ol reduced the attraction number and thus was an inhibitor; and (6Z,9Z)-6,9-tricosadiene addition did not affect the attraction number and thus was an inactive ingredient. Consequently, only (9Z)-9,13-tetradecadien-11-ynal (1) was identified as a *Stenoma catenifer* sex pheromone (Jocelyn G. Millar et al., Tetrahedron Letters 2008, 49, 4820-4823, and Mark S. Hoddle et al., J. Econ. Entomol. 2009, 102(4), 1460-1467).

On the other hand, (9E)-9,13-tetradecadien-11-ynal (2) contained in the composition of the present invention is a geometric isomer of (9Z)-9,13-tetradecadien-11-ynal (1), is not a natural pheromone substance of *Stenoma catenifer*, and is not reported to be extracted from *Stenoma catenifer* (Tetrahedron Letters 2008, 49, 4820-4823).

Whether a compound similar in structure to a pheromone substance functions in the same manner as the pheromone substance or not differs from insect pest to insect pest. There is reported even a case in which the compound functions as an inhibitor. For example, in the case of *Stenoma catenifer*, the similar compound (9Z)-9,13-tetradecadien-11-yn-1-ol, which has the same main skeleton as that of the sex pheromone (9Z)-9,13-tetradecadien-11-ynal (1), but differ from it only in a functional group, is an attraction inhibitor. For example, in the case of tomato fruit borer (*Neoleucinodes elegantalis*), which is an insect pest of South American tomatoes, (11E)-11-hexadecenol is a sex pheromone main component, and (3Z,6Z,9Z)-3,6,9-tricosatriene is a sex pheromone secondary component. Addition of (11Z)-11-hexadecenol, which is a geometric isomer of a sex pheromone main component (11E)-11-hexadecenol, is reported to greatly reduce the attracted number (Aivle Cabrera, J. Chem. Ecol. 2001, 27(10), 2097). Thus, the effects of similar compounds and geometric isomers of sex pheromone substances of insect pests on the attraction of insect pests differ from insect pest to insect pest, and therefore it is necessary to confirm the effects by actual attraction tests.

(9Z)-9,13-tetradecadien-11-ynal (1) and (9E)-9,13-tetradecadien-11-ynal (2) are preferably artificially synthesized from a viewpoint of economy.

(9Z)-9,13-Tetradecadien-11-ynal (1) can be produced, for example, by a method comprising steps of: reacting 4-penten-2-ynal with a triarylphosphonium dialkoxyalkylide compound through a Wittig reaction to obtain a (5Z)-14,14-dialkoxy-1,5-tetradecadien-3-yn compound; and hydrolyzing the obtained (5Z)-14,14-dialkoxy-1,5-tetradecadien-3-yn compound.

On the other hand, (9E)-9,13-tetradecadien-11-ynal (2) can be prepared, for example, by a method comprising steps of: reacting 4-penten-2-yal with triarylphosphonium dialkoxyalkylide compound through a Wittig reaction (Schlosser modification) to obtain a (5E)-14,14-dialkoxy-1,5-tetradecadien-3-yn compound; and hydrolyzing the obtained (5E)-14,14-dialkoxy-1,5-tetradecadien-3-yn compound.

The mixing ratio of (9Z)-9,13-tetradecadien-11-ynal (1) to (9E)-9,13-tetradecadien-11-ynal (2) is not particularly limited as long as male adults are attracted. The mass ratio of (9Z)-9,13-tetradecadien-11-ynal (1) to (9E)-9,13-tetradecadien-11-ynal (2) is preferably from 100:0.5 to 100:600, more preferably from 100:1 to 100:400, still more preferably from 100:10 to 100:350, and particularly preferably from 100:33 to 100:300.

(9Z)-9,13-Tetradecadien-11-ynal (1) and (9E)-9,13-tetradecadien-11-ynal (2) may contain impurities which are unavoidable in their production.

The above-mentioned bioactive composition may comprise an optional additive. Examples of the optional additive includes an antioxidant such as 2,6-di-tert-butyl-4-methylphenol (BHT), butylhydroxytoluene, butylhydroxyanisole, hydroquinone, and vitamin E; and an ultraviolet absorber such as 2-hydroxy-4-octyloxybenzophenone, and 2-(2'-hydroxy-3'-tert-butyl-5'-methylphenyl)-5-chlorobenzotriazole (HBMCBT). When the bioactive composition is used as a sustained release preparation, the additive may be a compound which is released together with (9Z)-9,13-tetradecadien-11-ynal (1) and (9E)-9,13-tetradecadien-11-ynal (2), or a compound which remains without being released.

The content of each additive in the bioactive composition is, for example, from 0.5 to 50% by mass of an antioxidant, and from 0.5 to 50% by mass of an ultraviolet absorber, relative to the total amount of (9Z)-9,13-tetradecadien-11-ynal (1) and (9E)-9,13-tetradecadien-11-ynal (2).

Next, a sustained release preparation comprising the bioactive composition and a carrier or container for sustainedly releasing (9Z)-9,13-tetradecadien-11-ynal (1) and (9E)-9,13-tetradecadien-11-ynal (2) in the bioactive composition will be described.

The release of (9Z)-9,13-tetradecadien-11-ynal (1) and (9E)-9,13-tetradecadien-11-ynal (2) into a field is not particularly limited as long as the insect pests can be controlled. There are used, for example, a sustained release preparation comprising a carrier impregnated with the above-mentioned bioactive composition; and a sustained release preparation comprising a container such as a cap, a tube, a capsule, an ampoule, a can or a bag, each containing the above-mentioned bioactive composition.

The sustained release preparation may be any preparation capable of sustainedly releasing an active ingredient such as a pheromone compound from a carrier or a container or the like little by little for a desired period of time for pest control or the other purpose. Examples of the sustained release preparation include a lure preparation, a reservoir type preparation, a matrix preparation, an aerosol preparation, and a scattering type preparation. It is sufficient that an active ingredient such as a pheromone compound can be released, for example, into a field, regardless of whether it is actively and passively released from a carrier, a container or the like.

A sustained release preparation for controlling *Stenoma catenifer* comprises a bioactive composition, and a carrier or container for sustainedly releasing (9Z)-9,13-tetradecadien-11-ynal (1) and (9E)-9,13-tetradecadien-11-ynal (2) in the bioactive composition.

A sustained release preparation comprising a carrier may be produced by a well-known method such as kneading or impregnation of the bioactive composition into a carrier. The shape and size of the carrier are variable depending on the type and amount of application. For example, a handheld preparation comprising a ring-shaped carrier has a ring diameter of preferably from 0.01 to 5 m. A scattering preparation comprising a particulate carrier having a spherical or oval shape has a particle diameter (a long side in the case of an ellipse) of preferably from 0.01 to 10 cm. The amount of the bioactive composition supported on the carrier is variable depending on the type and amount of application. It is preferably from 0.01 mg to 100 g, more preferably from 1 mg to 10 g, per preparation.

A sustained release preparation comprising a container may be produced by a well-known method. It may be produced, for example, by the method comprising steps of: injecting the bioactive composition or the like into a polymer tube, and sealing both ends of the tube; or by the method comprising steps of filling a can with the bioactive composition or the like, and attaching a sprayable valve to the can.

An optional diluent may be used for the sustained release preparation comprising a container. Examples of the diluent include hydrocarbons such as hexane, heptane, octane, nonane, decane and toluene; esters such as ethyl acetate and n-butyl acetate; ketones such as acetone and methyl ethyl ketone; ethers such as diethyl ether and dibutyl ether; nitriles such as acetonitrile and propionitrile; aprotic polar solvents such as N,N-dimethylformamide; mineral oils such as kerosene, liquid paraffin, amber oil and creosote oil; vegetable oils such as castor oil, linseed oil, salad oil, corn oil, soybean oil, sesame oil, rapeseed oil, safflower oil, sunflower oil, palm oil, olive oil, peanut oil, almond oil, grapeseed oil, jojoba oil, rose hip oil, avocado oil, hazelnut oil and orange oil; animal oils such as fish oil, lanolin oil, squalane oil, egg yolk oil, liver oil, horse oil and mink oil; and synthetic oils such as ester oil.

The amount of the diluent to be added is preferably from 0 to 10,000 parts by mass, relative to 100 parts by mass of the total amount of (9Z)-9,13-tetradecadien-11-ynal (1) and (9E)-9,13-tetradecadien-11-ynal (2).

A propellant is used for the sustained release preparation comprising a can as a container. Examples of the propellant include liquefied petroleum gas such as propane, propylene, n-butane and isobutane; liquefied gas such as dimethyl-ether (hereinafter also referred to as "DME"); halogenated carbon gas such as HFC-152a, HFC-134a, HFO-1234yf and HFO-1234ze; carbon dioxide gas; nitrogen gas; and compressed gas such as compressed air. The propellant may be used singly or in combination of two or more.

A mass ratio of a total amount of (9Z)-9,13-tetradecadien-11-ynal (1), (9E)-9,13-tetradecadien-11-ynal (2), the above additive and diluent to an amount of the propellant is preferably from 80:20 to 25:75, more preferably from 45:55 to 65:35, from the viewpoint of control effect.

The sustained release preparation comprising a can as a container has a filling amount of preferably from 0.01 mg to 500 g, more preferably from 1 mg to 200 g, from the viewpoint of control effect.

The sustained release preparation comprising a tubular container is appropriate because of its long period of release and uniform release of (9Z)-9,13-tetradecadien-11-ynal (1), (9E)-9,13-tetradecadien-11-ynal (2), and the like. The inner diameter of the tubular container is preferably from 0.01 to 5.0 mm, and the wall thickness thereof is preferably from 0.05 to 3.0 mm, from the viewpoint of maintaining an appropriate release rate.

When the number of installation locations of the preparations is reduced without changing the release amount per unit area, it is desirable to change the length of the sustained release preparation comprising the tubular container without changing the filling amount per unit length of the sustained release preparation comprising the tubular container. The length of the sustained release preparation comprising the tubular container is preferably from 0.2 to 100 m, more preferably from 0.5 to 20 m, and still more preferably from 1 to 10 m. However, this does not apply to the case where two or more of the sustained release preparations comprising a tubular container are connected for use. The filling amount per 1 m of the sustained release preparations comprising a tubular container in this case is preferably from 0.005 to 5.5 g.

The carrier which the sustained release preparation comprises is not particularly limited as long as it is made of a material capable of stably retaining the bioactive composition and capable of releasing at least (9Z)-9,13-tetradecadien-11-ynal (1) and (9E)-9,13-tetradecadien-11-ynal (2) in a bioactive composition for a certain period of time. Examples of such a material include natural rubbers such as cis-polyisoprene; synthetic rubbers such as isoprene rubber and butadiene rubber; polyolefins such as polyethylene or polypropylene; sodium metasilicate; silica gel; quartz; polylactic acid; polycaprolactone; polyhydroxyalkanoate; polyglycolic acid; polybutylene succinate; modified polyvinyl alcohol; casein; modified starch; polyhydroxyalkanoic acids such as polyhydroxybutyric acid; polysaccharide derivatives such as cellulose and acetylcellulose; and minerals such as zeolites.

The container which the sustained release preparation comprises is not particularly limited as long as it is made of a material capable of releasing at least (9Z)-9,13-tetradecadien-11-ynal (1) and (9E)-9,13-tetradecadien-11-ynal (2) in the bioactive composition for a certain period of time. Examples of the container include containers made of a polymer and containers made of a metal.

As the polymer, a polymer allowing (9Z)-9,13-tetradecadien-11-ynal (1), (9E)-9,13-tetradecadien-11-ynal (2) and the like to penetrate through the polymer membrane and release them to the outside of the polymer membrane at an appropriate rate is preferable. Examples of the polymer include natural rubbers such as cis-polyisoprene; synthetic rubbers such as isoprene rubber, butadiene rubber and acrylonitrile-butadiene rubber (NBR); polyolefins such as polyethylene and polypropylene; copolymers containing 80% by weight or more of ethylene such as an ethylene-vinyl acetate copolymer and an ethylene-acrylate ester copolymer; biodegradable plastics such as polylactic acid, polycaprolactone, polyhydroxyalkanoate and cellulose; polyvinyl acetate; polyvinyl chloride; and polytetrafluoroethylene. The synthetic rubbers, the ethylene-vinyl acetate copolymer and polylactic acid are preferable from the viewpoint of economy and versatility. These polymers may be used as a spray container by increasing the film thickness to suppress permeation.

As the metal, there may be used any metal that can be used for spraying or scattering. Examples of the metal include aluminum, stainless steel and steel.

Next, there will be described a method for controlling *Stenoma catenifer*, comprising steps of installing the sustained release preparation comprising a bioactive composition comprising (9Z)-9,13-tetradecadien-11-ynal (1) and (9E)-9,13-tetradecadien-11-ynal (2), and a carrier or container for sustainedly releasing the (9Z)-9,13-tetradecadien-11-ynal (1) and (9E)-9,13-tetradecadien-11-ynal (2) in the bioactive composition in a field to release the (9Z)-9,13-tetradecadien-11-ynal (1) and (9E)-9,13-tetradecadien-11-ynal (2) in the sustained release preparation.

Examples of the method for controlling *Stenoma catenifer* include mass trapping, attract and kill, push-pull, attract and infect, and mating disruption. According to the invention, the sustained release preparation is particularly preferably suitable for these control methods directed to *Stenoma catenifer* present in the field.

The release of (9Z)-9,13-tetradecadien-11-ynal (1) and (9E)-9,13-tetradecadien-11-ynal (2) in the composition bioactive to *Stenoma catenifer* into a field is not particularly limited as the insect pests can be controlled. It is desirable to carry out the release in an active or passive manner, for example, by using the above-described sustained release preparation. Examples of the release in the active manner include spraying or scattering from cans, spray bottles, sprinklers and irrigation facilities. Examples of the release in the passive manner include permeation or release (sustained release) from a container or carrier.

The installation of the sustained release preparation in a field is not particularly limited. For example, the installation density of the sustained release preparations is from 0.10 to 2000 installation locations/ha, preferably from 0.25 to 1000 installation locations/ha, with the proviso that the preparations are uniformly installed in the field to be controlled.

The amount released from one installation location cannot be generally said because of the dependency on the field environment, weather conditions and the like. It is not particularly limited as long as it may be such an amount to allow uniform float in the field. The amount released is preferably from 0.001 to 20 g/day/ha.

As described above, it is possible to control *Stenoma catenifer*, which is a significant insect pest of avocado in North, Central and South America.

EXAMPLES

Hereinafter, the invention will be more specifically described with reference to Examples. However, it should not be construed that the invention is limited to or by Examples.

Example 1

A composition bioactive to *Stenoma catenifer* was prepared by adding BHT (2,6-di-tert-butyl-4-methylphenol) and HBMCBT (2-(2'-hydroxy-3'-tert-butyl-5'-methylphenyl)-5-chlorobenzotriazole) as stabilizers to 1.2 mg of the mixed liquid obtained by mixing (9Z)-9,13-tetradecadien-11-ynal (1) and (9E)-9,13-tetradecadien-11-ynal (2) at a mass ratio of 100:300, in such amounts to make each concentration of the BHT and HBMCBT to be 2% by mass to obtain the bioacitve composition. A rubber cap made of isoprene was allowed to carry the composition to produce a sustained release preparation.

A white adhesive trap was used for evaluation of the sustained release preparation. As shown in FIG. 1, the white adhesive trap comprises a roof and a bottom plate, and insect pest entrances are narrowly formed. An adhesive substance is placed to the upper surface of the bottom plate, and the sustained release preparation A is directly mounted on the adhesive surface for use. In other words, the white adhesive trap has the structure in which only insect pests that come close to the sustained release preparation are captured, and the capture of untargeted insect pests are avoided as much as possible.

In the period of from September 23 and Nov. 25, 2019, the traps containing the respective sustained release preparations were installed in the orchards in which *Stenoma catenifer* lived. Adult male insect pests captured and killed in each trap were counted every 7 days. The control effect was evaluated by determining the relative value of the number of the insect pests captured by the sustained release preparation of Example 1 when regarding the total number of insect pests captured by the sustained release preparation of later-described Example 2 as 100. The results are shown in Table 1.

Example 2

A sustained release preparation was produced and evaluated for the control effect in the same manner as in Example 1 except that 0.6 mg of the mixed liquid obtained by mixing (9Z)-9,13-tetradecadien-11-ynal (1) and (9E)-9,13-tetradecadien-11-ynal (2) at a mass ratio of 100:100 was used. The results are shown in Table 1.

Example 3

A sustained release preparation was produced and evaluated for the control effect in the same manner as in Example 1 except that 0.4 mg of the mixed liquid obtained by mixing (9Z)-9,13-tetradecadien-11-ynal (1) and (9E)-9,13-tetradecadien-11-ynal (2) at a mass ratio of 100:33 was used. The results are shown in Table 1.

Comparative Example 1

A sustained release preparation was produced and evaluated for the control effect in the same manner as in Example 1 except that 0.3 mg of (9Z)-9,13-tetradecadiene-11-ynal (1) was used in place of 1.2 mg of the mixed liquid in Example 1. The results are shown in Table 1.

TABLE 1

| | mixing ratio (mass ratio) | | |
|---|---|---|---|
| | (9Z)-9,13-tetradecadien-11-ynal | (9E)-9,13-tetradecadien-11-ynal | total capture number (relative value) |
| Example1 | 100 | 300 | 99 |
| Example2 | 100 | 100 | 100 |
| Example3 | 100 | 33 | 94 |
| Comp. Ex. 1 | 100 | 0 | 70 |

In all tests of Examples 1 to 3 and Comparative Example 1, each amount of (9Z)-9,13-tetradecadien-11-ynal (1) was the same and 0.3 mg.

Each attractant in Examples 1-3 exhibited the larger number of male adult insect pests of *Stenoma catenifer* than the attractant in Comparative Example 4. Thus, increase in the total number of the captured insect pests by addition of (9E)-9,13-tetradecadien-11-ynal (2) was confirmed.

The invention claimed is:

1. A composition bioactive to *Stenoma catenifer*, the composition comprising (9Z)-9,13-tetradecadien-11-ynal and (9E)-9,13-tetradecadien-11-ynal in an effective ratio to control the *Stenoma catenifer*.

2. The composition bioactive to a *Stenoma catenifer* according to claim 1, wherein a mass ratio of the (9Z)-9,13-tetradecadien-11-ynal to the (9E)-9,13-tetradecadien-11-ynal is from 100:0.5 to 100:600.

3. A sustained release preparation for controlling *Stenoma catenifer*, the preparation comprising:
the composition according to claim 1, and
a carrier or container that sustainedly releases the (9Z)-9,13-tetradecadien-11-ynal and the (9E)-9,13-tetradecadien-11-ynal.

4. A method for the controlling *Stenoma catenifer*, the method comprising a step of installing the sustained release preparation according to claim 3 in a field to release the (9Z)-9,13-tetradecadien-11-ynal and the (9E)-9,13-tetradecadien-11-ynal into the field.

5. A sustained release preparation for controlling *Stenoma catenifer*, the preparation comprising:
the composition according to claim 2, and
a carrier or container that sustainedly releases the (9Z)-9,13-tetradecadien-11-ynal and the (9E)-9,13-tetradecadien-11-ynal.

6. A method for the controlling *Stenoma catenifer*, the method comprising a step of installing the sustained release preparation according to claim 5 in a field to release the (9Z)-9,13-tetradecadien-11-ynal and the (9E)-9,13-tetradecadien-11-ynal into the field.

\* \* \* \* \*